(12) United States Patent
Medina Rivero

(10) Patent No.: US 10,524,507 B2
(45) Date of Patent: Jan. 7, 2020

(54) DEVICE FOR TRYING ELECTRONIC CIGARETTE LIQUIDS

(71) Applicant: Armando Medina Rivero, Seville (ES)

(72) Inventor: Armando Medina Rivero, Seville (ES)

(*) Notice: Subject to any disclaimer, the term of this patent is extended or adjusted under 35 U.S.C. 154(b) by 246 days.

(21) Appl. No.: 15/114,084

(22) PCT Filed: Apr. 9, 2014

(86) PCT No.: PCT/ES2014/070280
§ 371 (c)(1),
(2) Date: Jul. 26, 2016

(87) PCT Pub. No.: WO2015/124807
PCT Pub. Date: Aug. 27, 2015

(65) Prior Publication Data
US 2017/0000191 A1 Jan. 5, 2017

(30) Foreign Application Priority Data

Feb. 21, 2014 (ES) .................................. 201430232

(51) Int. Cl.
*A24F 47/00* (2006.01)
*A61M 15/06* (2006.01)
*F22B 1/28* (2006.01)

(52) U.S. Cl.
CPC ........... *A24F 47/008* (2013.01); *A61M 15/06* (2013.01); *F22B 1/285* (2013.01);
(Continued)

(58) Field of Classification Search
CPC .. A24F 47/008; A61M 11/042; A61M 11/044; A61M 15/06
See application file for complete search history.

(56) References Cited

U.S. PATENT DOCUMENTS

| 5,322,075 A | 6/1994 | Seethharama |
| 5,620,524 A * | 4/1997 | Fan ............................ B01J 4/00 118/715 |

(Continued)

FOREIGN PATENT DOCUMENTS

| CN | 203087527 U | 7/2013 |
| CN | 203378558 U | 1/2014 |

(Continued)

OTHER PUBLICATIONS

CN203378558_English Translation.*

*Primary Examiner* — Tulsidas C Patel
*Assistant Examiner* — Marcus E Harcum
(74) *Attorney, Agent, or Firm* — Galbreath Law Offices, P.C.; John A. Galbreath

(57) ABSTRACT

The invention relates to a device that can be used to try electronic cigarette liquids, intended for the retail sale of electronic cigarettes, providing a system that allows the end client to try different electronic cigarettes without having to put together a complete assembly for each type of liquid, said device taking the form of a block provided internally with a set of clearomizers and vacuum pumps that convey the aroma into a single tube to the exterior. Alternatively, it can be assembled with a single vacuum pump or without any vacuum pump, using instead direction aspiration, or manual selection prior to the selected test or aspiration.

4 Claims, 8 Drawing Sheets

(52) U.S. Cl.
CPC ............... *A61M 2205/588* (2013.01); *A61M 2205/8206* (2013.01); *A61M 2205/8256* (2013.01); *A61M 2209/02* (2013.01)

(56) References Cited

U.S. PATENT DOCUMENTS

| | | | |
|---|---|---|---|
| 5,916,524 | A | 6/1999 | Tisone |
| 2006/0047368 | A1* | 3/2006 | Maharajh .................. F22B 1/28 700/283 |
| 2006/0196518 | A1* | 9/2006 | Hon ...................... A24F 47/002 131/360 |
| 2013/0160780 | A1* | 6/2013 | Matsumoto ........... A24F 47/002 131/329 |
| 2013/0199528 | A1* | 8/2013 | Goodman ............... F22B 1/282 128/203.26 |
| 2013/0200463 | A1* | 8/2013 | Becker ................ H01L 27/0207 257/369 |
| 2014/0261488 | A1* | 9/2014 | Tucker .................. A24F 47/008 131/328 |
| 2015/0047662 | A1* | 2/2015 | Hopps ................... A24F 47/008 131/329 |
| 2015/0053217 | A1* | 2/2015 | Steingraber ........... A24F 47/008 131/329 |
| 2016/0325858 | A1* | 11/2016 | Ampolini .............. A24F 47/008 |
| 2018/0153208 | A1* | 6/2018 | Schaller ................ A24F 47/008 |

FOREIGN PATENT DOCUMENTS

| | | |
|---|---|---|
| EP | 1618803 | 1/2006 |
| WO | WO 2005053444 | 6/2005 |

\* cited by examiner

DEVICE FOR TRYING ELECTRONIC CIGARETTE LIQUIDS

PURPOSE OF INVENTION

The present invention, as expressed in the title of this specification, is to provide a device which allows a person to perform tests or "tastings" of different e-liquids without requiring the presence of any operator or assistant.

The present invention finds its scope in the retail trade of e-cigarettes, consumable e-liquids and other replacement features.

BACKGROUND AND STATE OF THE ART

As is known, users are familiar with and increasingly use electronic devices that replace or represent an alternative to tobacco.

Such devices are designed for vaporizing a rechargeable e-liquid content in an atomizer, when the user inhales through them, causing the expulsion of vapour that imitates traditional tobacco smoke in order for the smoker or user to experience a similar effect.

In terms of the state of the art in the field, points of sale for e-cigarettes and consumables and mainly the e-liquid inserted into them are sold in such a way that the only way to carry out a taste or nicotine level test is by introducing the e-liquid into the e-cigarette itself in order to carry out the corresponding enjoyment test without the opportunity being available to carry out a smell test independently of this.

In this regard, it proves complicated to perform a full tasting at the point of sale given that there are thousands of flavours and/or different levels of nicotine on the market. The test is therefore usually carried by providing the customer with as many e-cigarettes and flavours as they want to try, with these being made available with an extra single nozzle to use in order to ensure hygiene with each client's aspiration.

However, in regard to the state of the art, the "Device for testing e-cigarette e-liquids" provides a machine that allows straightforward operation which enables smell and taste tests to be carried out on different e-cigarette e-liquids, without changing the e-cigarette or having to change the atomizer in this, by selecting the liquid concerned as chosen by the user in a completely independent way, without requiring assistance and ensuring the hygiene of the test.

INVENTION DISCLOSURE

Disclosure for the invention "Device for testing e-cigarette e-liquids" can be provided by a description of the following components:

- Atomiser or component designed to contain the e-liquid in question and produce vapour, equal in quantity to that of e-liquids to be submitted for the test.
- Vacuum pump for each of the atomizers in order to draw air from each atomizer and expel it through the conduits for this purpose.
- Battery supplying the corresponding voltage to the previous component, atomizer and other electricity consuming components that can incorporated into the set.
- Battery power supply or set of electric power consumption components that can run directly off the electricity network.
- Control panel based on an analogue or digital system provided with the corresponding automation that allow the selection of the function to be performed and includes the selection or testing between different liquids.

Alternatively, assembly can be carried out using one single pump to perform the aspiration of the aroma released by the atomizer selected, or even by eliminating the vacuum pump/s so that the display presents as many suction ducts as atomizers contained inside it that are activated by the user's own aspiration using a pressure switch, flow switch or a selection button and close circuit.

DESCRIPTION OF FIGURES

To complement the description being made and in order to assist in a better understanding of the characteristics of the invention according to preferable examples of a practical design for this, a set of drawings has been attached as an integral part of this description and in which, for illustrative and unlimited purposes, the following has been represented.

In the above figures, the following key components can be highlighted:

1. Atomizer provided with e-liquid deposit.
2. Vacuum pumps
3. Check valves.
4. Battery that can operate independently.
5. Conventional power supply.
6. Control panel.
7. Power button.
8. Selection buttons and timings.
9. User testing nozzle.
10. Test tube or straw.
11. Solenoid valve.
12. Diodes.
13. Pressure switch.
14. Flow switch.
15. Mains socket.
16. Voltage regulator.
17. Timer.

EXAMPLE OF PREFERRED DESIGN

Figure 1:
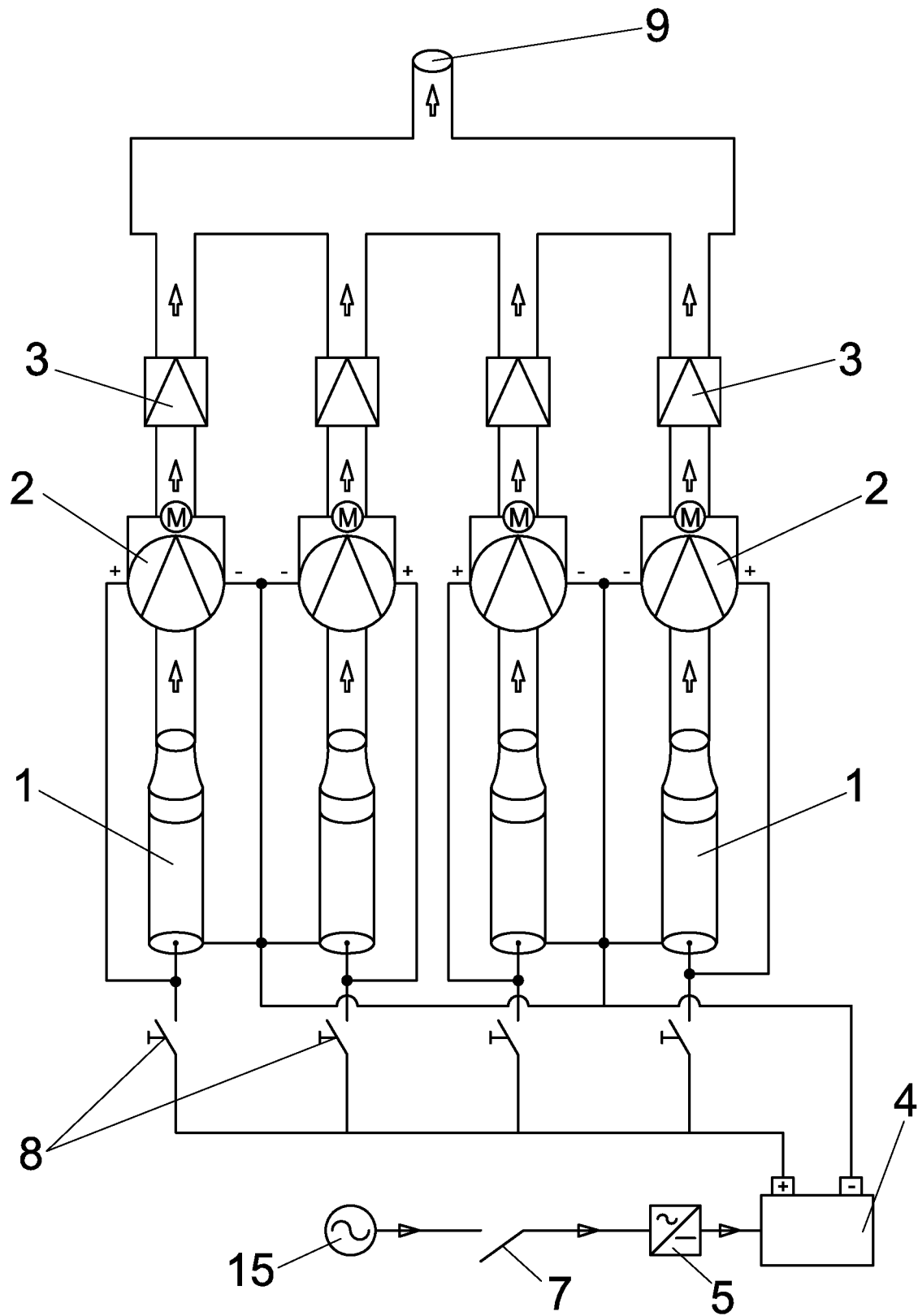
FIG. 1. Main diagram of "Device for testing e-cigarette e-liquids" provided with several vacuum pumps.
Figure 2:
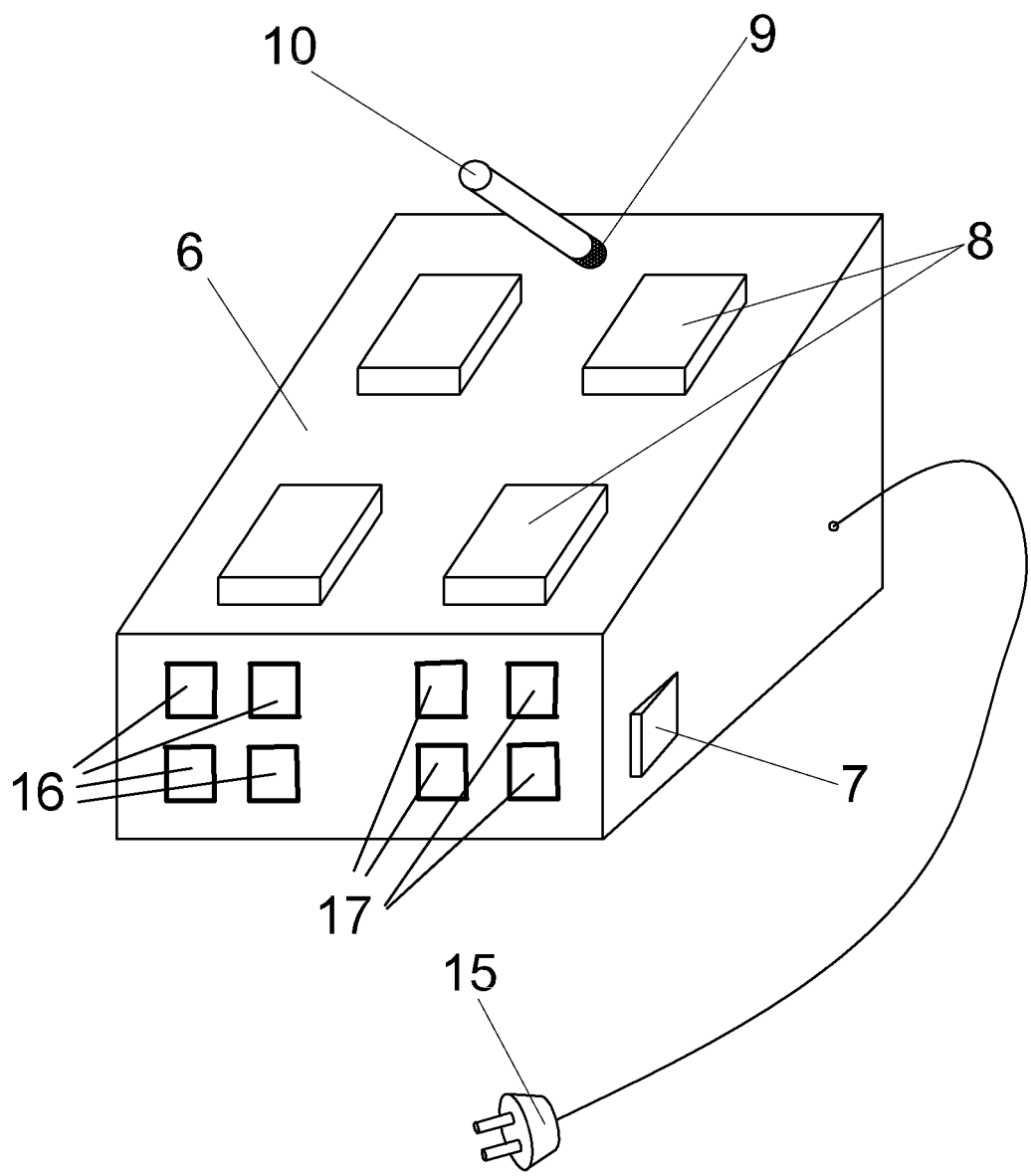
FIG. 2. Main view of "Device for testing e-cigarette e-liquids".

As a preferred design for "Device for testing e-cigarette e-liquids" provided with several vacuum pumps in the light of FIG. 1 and FIG. 2 shows how the same process is carried out by combining the following components Set of atomizers (1) vacuum pumps (2) and check valves (3) preventing the mixture of e-liquids depending on the quantity of blocks or columns and the variety of flavours to be contained by the set, in this case four.

Battery (4) of the proper voltage.

Conventional power supply (5) depending on plug or socket (15) of 125 or 220 volts.

Control Panel (6) incorporating different automatic devices such as power button (7), e-liquids selection button (8), voltage regulators (16) to deliver supply to the different components, timers (17) to limit the test duration time in the form of an example of 5 seconds, etc.

The system is complemented with the corresponding lines that end in a single output for the user in the form of a fixed nozzle (9) on which is mounted a single use test tube or straw (10) for carrying out the taste or smell test in order to ensure hygiene for each customer.

Example of Alternative Design for Common Suction Pump

Figure 3:
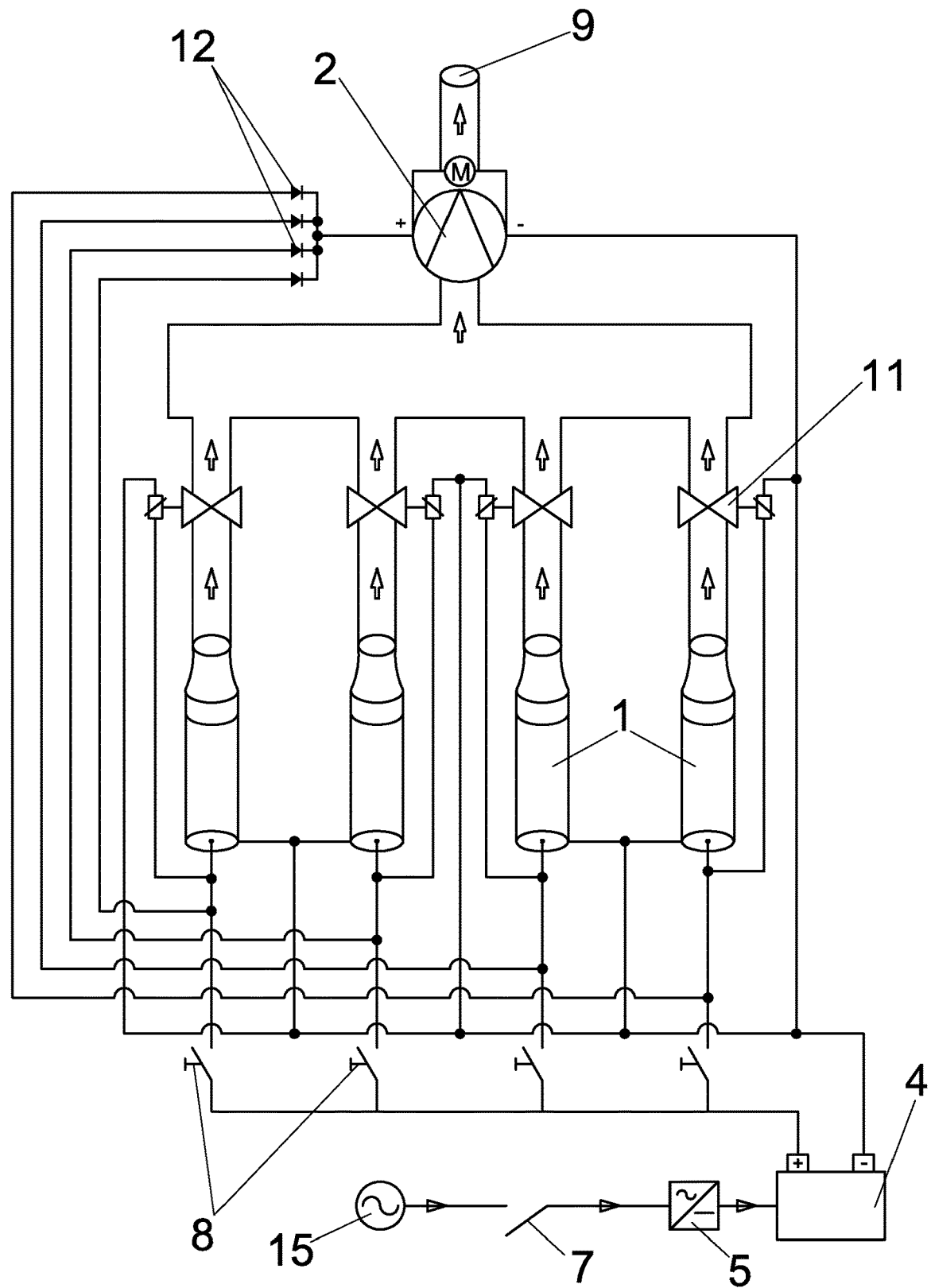
FIG. 3. Main diagram of "Device for testing e-cigarette e-liquids" provided with a single vacuum pump.

As an example of an alternative design 1 for "Device for testing e-cigarette e-liquids" by using a single pump, as shown in FIGS. 3 and 2, it can be observed how the same process is carried out by combining the following elements:

Set of atomizers (1), vacuum pump (2) and solenoid valve (11) which functions by opening for the testing of the selected e-liquid, depending on the quantity of blocks or columns and the variety of flavours to be contained by the set, in this case four.

Battery (4) of the proper voltage.

Diodes (12) that prevent multiple components be fed back at a time.

Conventional power supply (5) as plug or socket (15) for network of 125 or 220 volts.

Control Panel (6) incorporating different automatic devices such as power button (7), e-liquids selection button (8), voltage regulators (16) for adapting voltages to different elements, timers (17) to limit the test duration time in the form of an example of 5 seconds, etc.

The system is complemented with the corresponding lines that end in a single output for the user in the form of a fixed nozzle (9) on which is mounted a single use test tube or straw (10) for carrying out the taste or smell test in order to ensure hygiene for each customer, as shown in FIG. 2.

Example of Alternative Design without Vacuum Pump Through Direct Aspiration

Figure 4:
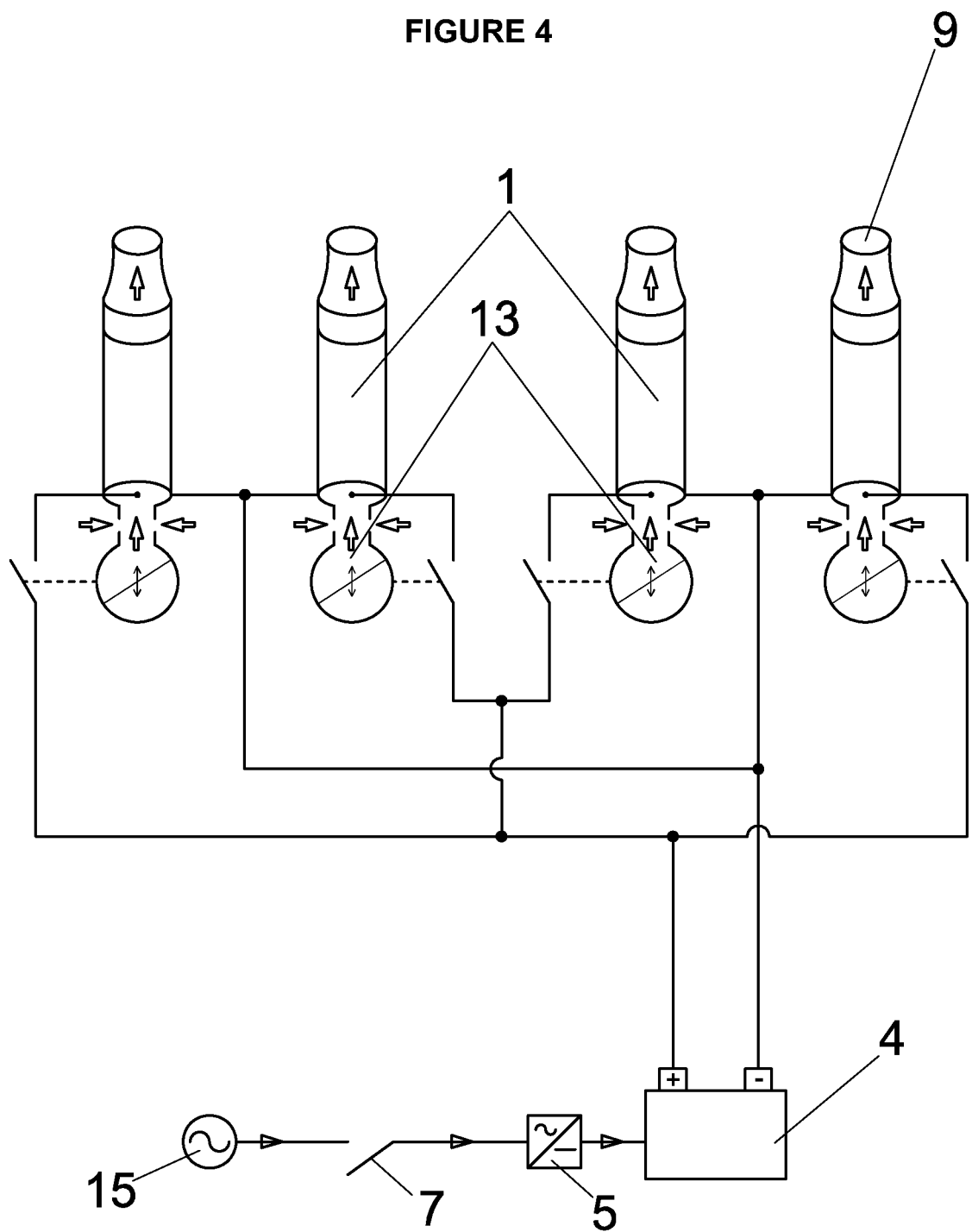
FIG. 4. Main diagram of alternative design for "Device for testing e-cigarette e-liquids" which does not include vacuum pumps with pressure switches.
Figure 5:
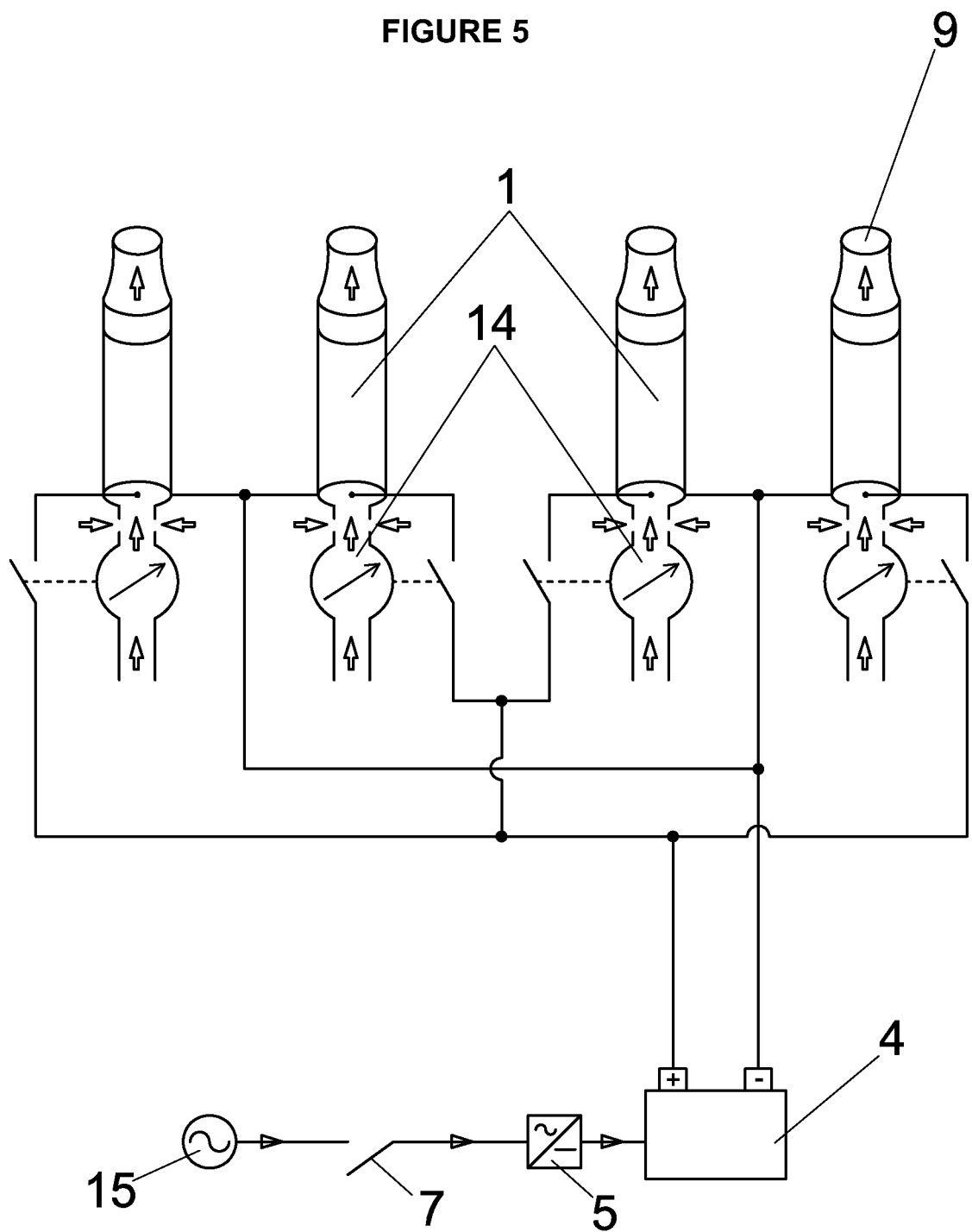
FIG. 5. Main diagram of alternative design for "Device for testing e-cigarette e-liquids" which does not include vacuum pumps with flow switches.
Figure 6:
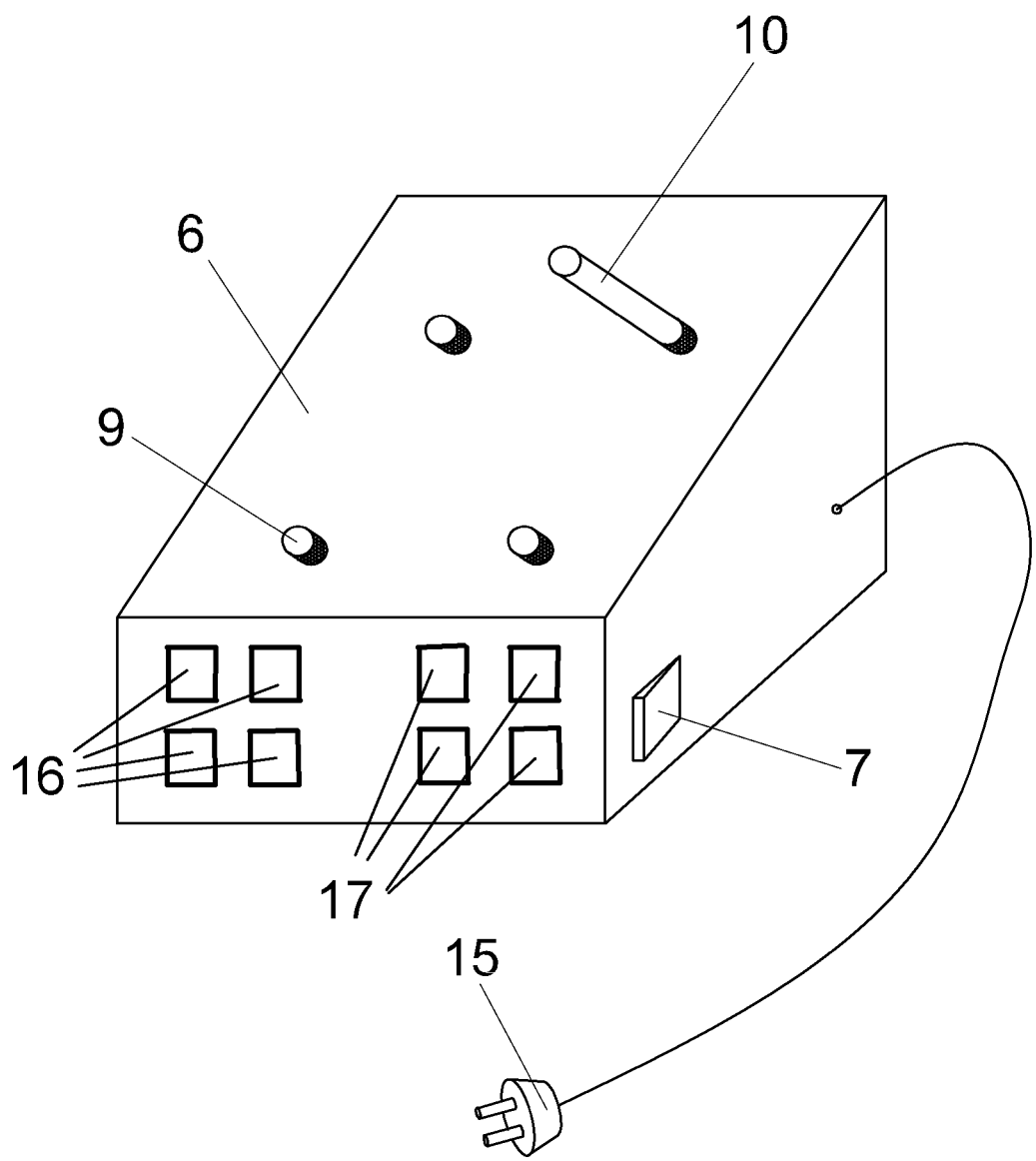
FIG. 6. Main view of "Device for testing e-cigarette e-liquids" that does not include suction pumps with pressure switches or flow switches FIG. 7. Main diagram of alternative design for "Device for testing e-cigarette e-liquids" which does not include vacuum pumps for manual operation.

As an example of alternative design 2 for "Device for testing e-cigarette e-liquids" without suction pump and by direct aspiration as shown in FIGS. 4, 5 and 6, it can be observed how this does not incorporate vacuum pumps, performs e-liquid intake by the conventional method through the user on the output of the selected atomizer (1), by using a pressure switch (13) or flow switch (14) as a physical component which upon detecting aspiration, and stops the electrical activation of the atomizer selected by the user.

Example of Alternative Design without Vacuum Pump by Manual Operation Selection

Figure 7:
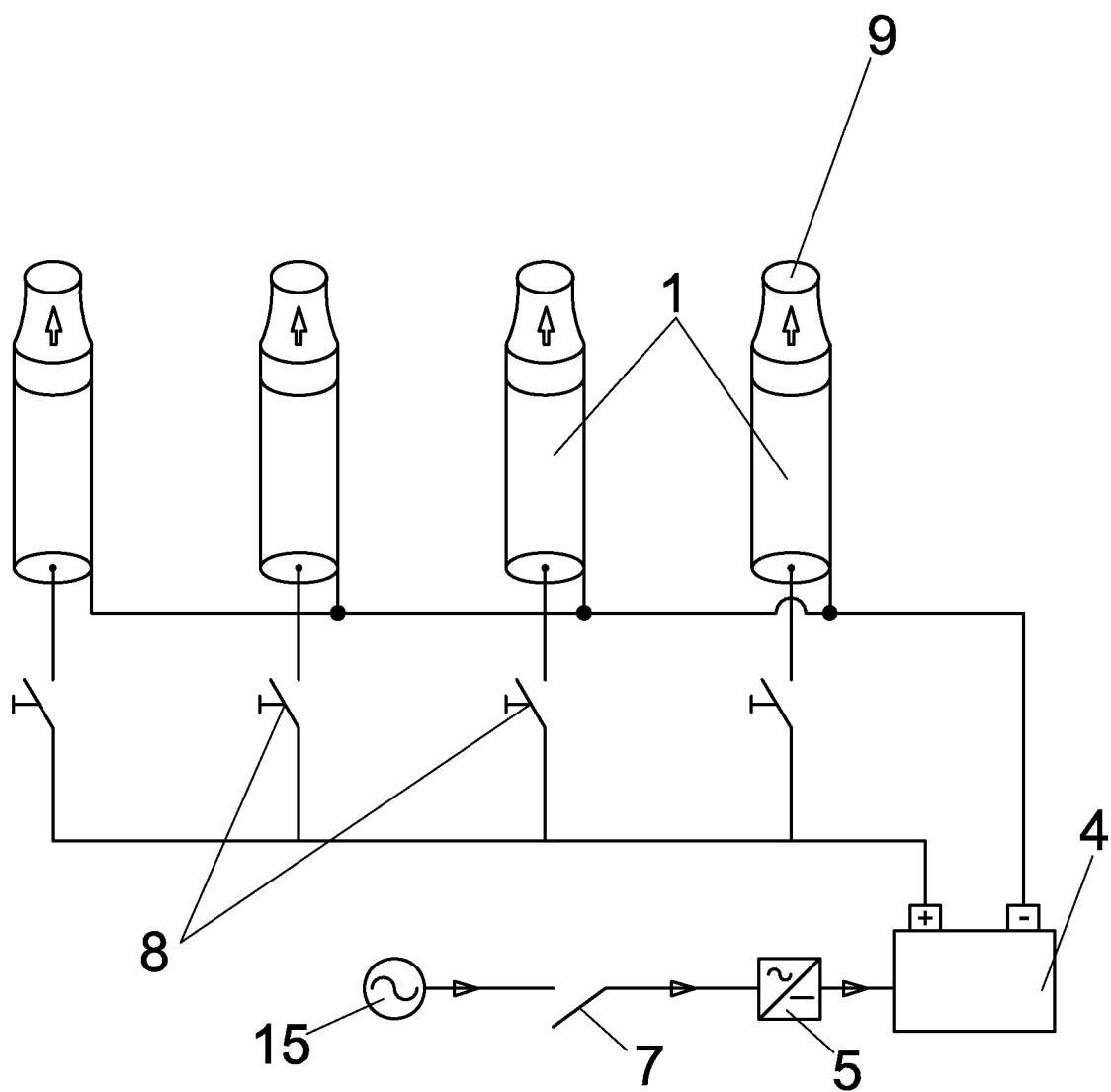
Figure 8:
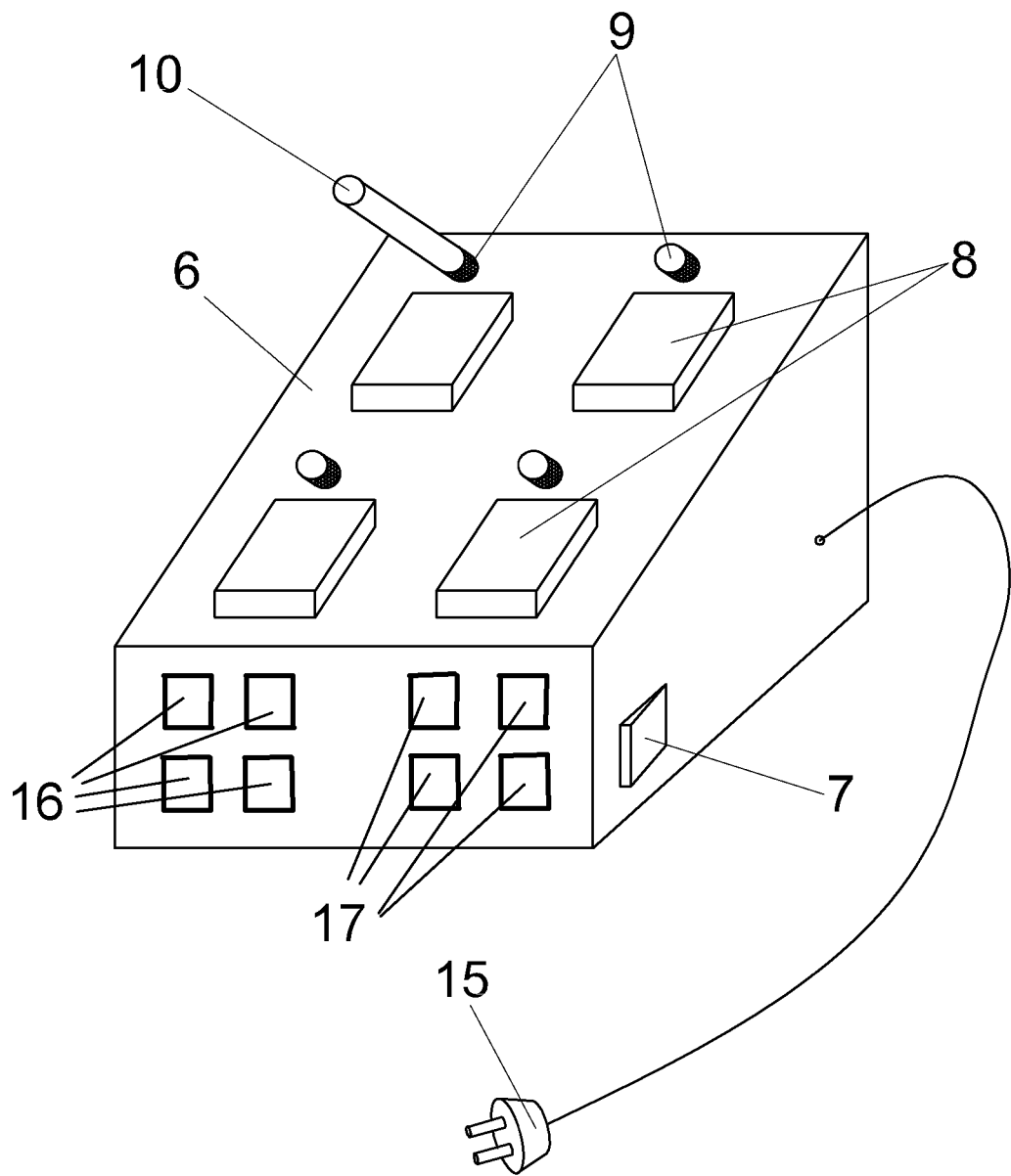
FIG. 8. Main view of manually-operated "Device for testing e-cigarette e-liquids"

As an example of alternative design 3 for "Device for testing e-cigarette e-liquids" without vacuum pump and provided with selection keyboard by manual operation as set out in FIGS. 7 and 8, it can be observed that the selection button (8) shorts the electric circuit and activates the function of the atomizer (1).

It is not considered necessary to extend this description in order for any expert in the field to understand the scope of the invention and the advantages that it can provide. The component features, dimensions, or implementation techniques, including its version of a digital panel for user interaction, may vary as long as this does not alter the essence of the invention.

The invention claimed is:

1. Device for testing e-cigarette e-liquids characterised by its operation on the basis of the combination of the following elements:
   a) four or more atomisers or component designed to contain cigarette liquids and to produce vapour through aspiration by a user,
   b) a battery that provides voltage corresponding to the atomisers,
   c) a battery power supply; vacuum pumps; check valves;
   d) a mains socket;
   e) a control panel incorporating power button, cigarette liquids selection button, a plurality of voltage regulators to deliver the power supply to the above cited components, and several timers to limit the test duration time;
   characterized by suction means consisting of a vacuum pump and check valve for each atomiser tasked with aspirating air and carrying it outwards through ducts that end in a single output for the user in the form of a fixed nozzle, on which is mounted a single use test tube or straw for carrying out the taste or olfactory test.

2. Device for testing e-cigarette e-liquids according to claim 1, characterized by channels for aspiration which is also carried out with a common vacuum pump, connected by a set of solenoid valves to a set of atomisers which operate by opening, cutting off or allowing air to pass, depending on which atomizer is actioned, for the test of the selected liquid, which is contained in one of the four atomisers and not separated from it, according to as many varieties of flavours that the device contains.

3. Device for testing electronic e-cigarette e-liquids according to claim 1, characterized by its aspiration is operated by the user, applied to the outlet of the atomiser selected, using pressure switches or flow switches which stop the electrical activation of the atomiser selected by the user, when aspiration is detected.

4. Device for testing electronic e-cigarette e-liquids according to claim 1, characterized by its aspiration is operated by the user, applied to the outlet of the atomiser selected, using a selection button for each atomiser which stops the electrical circuit when pressed and activates the operation of the same device.

* * * * *